United States Patent [19]
Axelsson et al.

[11] Patent Number: 5,888,995
[45] Date of Patent: Mar. 30, 1999

[54] STEROID ESTERS

[75] Inventors: Bengt Ingemar Axelsson, Genarp; Ralph Lennart Brattsand, Lund; Leif Arne Källström, S:a Sandby; Bror Arne Thalén, Bjärred, all of Sweden

[73] Assignee: Astra Aktiebolag, Sodertalje, Sweden

[21] Appl. No.: 493,733

[22] Filed: Jun. 22, 1995

Related U.S. Application Data

[63] Continuation-in-part of Ser. No. 94,100, Aug. 24, 1993, Pat. No. 5,614,514.

[30] Foreign Application Priority Data

Feb. 4, 1991 [SE] Sweden .................................. 9100342

[51] Int. Cl.$^6$ .............................. C07J 71/00; A61K 31/58
[52] U.S. Cl. ............................................... 514/174; 540/70
[58] Field of Search ................................ 540/70; 514/174

[56] References Cited

U.S. PATENT DOCUMENTS

| | | | |
|---|---|---|---|
| 3,048,581 | 8/1962 | Fried ................................. | 260/239.55 |
| 3,126,375 | 3/1964 | Ringold et al. .................... | 260/239.55 |
| 3,197,469 | 7/1965 | Fried ................................. | 260/239.55 |
| 3,357,974 | 12/1967 | Taub ................................. | 260/239.55 |
| 3,758,686 | 9/1973 | Sieger et al. ..................... | 424/241 |
| 3,796,701 | 3/1974 | Cimarusti ....................... | 260/239.55 D |
| 3,929,768 | 12/1975 | Brattsand et al. ............. | 260/239.55 D |
| 4,304,727 | 12/1981 | Heather et al. ................. | 260/397.45 |
| 4,693,999 | 9/1987 | Axelsson et al. ................. | 514/174 |
| 4,695,625 | 9/1987 | MacDonald ...................... | 540/63 |
| 4,835,145 | 5/1989 | MacDonald ...................... | 514/174 |

FOREIGN PATENT DOCUMENTS

| | | |
|---|---|---|
| 0054010 | 6/1982 | European Pat. Off. . |
| 0164636 | 6/1984 | European Pat. Off. . |
| 0127294 | 12/1984 | European Pat. Off. . |
| 0170642 | 2/1986 | European Pat. Off. . |
| 58-176485 | 4/1985 | Japan . |
| 139640 | 11/1973 | Norway . |
| 483720 | 8/1979 | Spain . |

OTHER PUBLICATIONS

Thalen et al. "Synthesis and Pharmacological Properties of some 16α, 17α–acetals of 16α–hydroxyhydrocortisone, 16α–hydroxyprednisolone and Fluorinated 16α–hydroxyprednisolones," Acta Pharm. Suec. 21, 109–124, 1984.

Perlman, et al. "Structure–cytotoxicity relations of some corticosteroids," Chem Abs. 67: 79235v, 1992.

Harget, A.J. "Classificatin of steroid partition coefficients by a pattern recognition technique," Chem Abs. 112: 235688u, 1992.

Flynn, G. L. "Structural approach to partitioning: estimation of steroid partition coefficients based upon molecular constitution," Chem Abs. 74: 130331x, 1992.

Primary Examiner—Mark L. Berch
Assistant Examiner—Bruck Kifle
Attorney, Agent, or Firm—White & Case LLP

[57] ABSTRACT

The invention concerns compounds of formula I

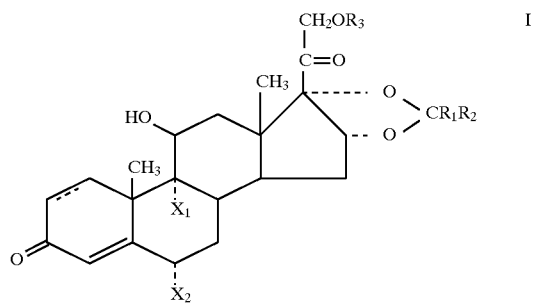

in which $R_1$ is hydrogen or a straight or branched hydrocarbon chain; $R_2$ is hydrogen or a straight or branched hydrocarbon chain; $R_3$ is acyl; $X_1$ is hydrogen, fluorine or chlorine; and $X_2$ is hydrogen, fluorine or chlorine. Also disclosed are processes for preparation of the compounds, pharmaceutical compositions containing them and methods employing the compounds in the treatment of inflammatory and allergic conditions.

14 Claims, No Drawings

STEROID ESTERS

This application is a continuation-in-part of application Ser. No. 08/094,100, filed Aug. 24, 1993, now U.S. Pat. No. 5,614,514.

BACKGROUND OF THE INVENTION

Glucocorticosteroids (GCS's) are valuable drugs for relief of asthma and rhinitis. It is widely accepted that GCS exert their therapeutic efficacy by anti-inflammatory and anti-anaphylactic actions within airway and lung tissue. The long-term oral use of GCS's is greatly hampered by severe side effects outside the lung. Accordingly, only a minor proportion of patients with asthma or rhinitis currently undergo oral GCS therapy; greater safety can be achieved by delivering GCS's by inhalation. However, the potent inhaled GCS's in current wide clinical use—beclomethasone 17α, 21-dipropionate and budesonide—have a rather narrow safety margin, and for both of these drugs unwanted GCS actions within the general circulation have been reported with the highest of the recommended doses for inhalation.

Liposomes are membrane-like vesicles consisting of series of concentric lipid bilayers alternating with hydrophilic compartments. Liposomes have been used as carriers for different kinds of pharmaceutically active compounds in order to improve drug delivery and to minimize side effects of the therapy.

Glucocorticosteroids can generally only be incorporated into liposomes at low concentrations and are poorly retained in the vesicles. Esterification of a GCS at the 21-position with fatty acids increases the degree of incorporation and the retention of the steroid in the vesicles. It has been shown that the fatty acid chain acts as a hydrophobic "anchor" which holds the steroid nucleus in the hydrated polar head groups of the phospholipid and thereby improves the interaction between the glucocorticosteroid and the liposome.

Liposome-encapsulated glucocorticosteroids for therapeutic use have been described (M. De Silva et al., Lancet 8130 (1979), 1320), and U.S. Pat. No. 4,693,999 describes liposomal formulations of glucocorticosteroids for inhalation.

SUMMARY OF THE INVENTION

The present invention relates to novel anti-inflammatory and antiallergic active compounds, to processes for their preparation, to pharmaceutical compositions containing them and to methods of treatment employing the compounds and compositions.

The object of the invention is to provide an anti-inflammatory, immunosuppressive and antiallergic glucocorticosteroid, or a pharmaceutical composition thereof, with high activity at the site of application, e.g. in the respiratory tract, on the skin, in the intestinal tract, in the joints or in the eye, by directing the drug to delimited target area, thereby inducing low glucocorticoid systemic effects.

A further object of the invention is to provide a pharmaceutical composition containing liposomes including a pharmacologically active steroid fatty acid ester of the invention in order to improve drug delivery and to minimize side effects of the therapy.

DETAILED DESCRIPTION OF THE INVENTION

One object of the present invention is to provide new GCS compounds. The new compounds are characterized by anti-inflammatory, immunosuppressive and antianaphylactic potency at the application site, and in particular by a markedly improved relationship between that potency and the ability to provoke GCS actions outside the treated region. The preferred mode of administration of the new compounds is by inhalation when the desired application site is within the airways.

Another object of the invention is to provide an anti-inflammatory and anti-allergic pharmaceutical composition containing steroid ester liposomes for local administration, e.g., to the respiratory tract. Such a composition provides for an improvement of the therapeutic properties of the steroid ester by a prolongation of the local retention in the airways and direction of the drug to specific target cells.

The compounds of the invention are characterized by the formula

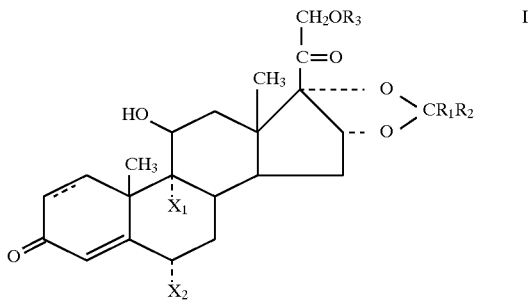

or a stereoisomeric component thereof, in which formula the 1,2-position is saturated or is a double bond;

$R_1$ is hydrogen or a straight or branched hydrocarbon chain having 1–4 carbon atoms;

$R_2$ is a hydrogen or a straight or branched hydrocarbon chain having 1–10 carbon atoms;

$R_3$ is acyl having a straight or branched, saturated or unsaturated hydrocarbon chain with 1–20 carbon atoms;

$X_1$ is hydrogen, fluorine or chlorine;

$X_2$ is hydrogen, flourine or chlorine; and further wherein
1) $R_1$ and $R_2$ are not simultaneously hydrogen;
2) $X_1$ and $X_2$ are not simultaneously hydrogen;
3) when the 1,2-position is a double bond, $R_1$ and $R_2$ are not simultaneously methyl groups;
4) when the 1,2-position is a double bond, $R_1$ is a hydrogen atom and $R_2$ is a straight or branched hydrocarbon chain having 1–10 carbon atoms, $R_3$ is acyl having 11–20 carbon atoms;
5) when the 1,2-position is saturated, $R_1$ and $R_2$ are methyl, $X_1$ is hydrogen and $X_2$ is fluorine, then $R_3$ is acyl having 6–20 carbon atoms.

The acyl is derived from $CH_3COOH$: acetic acid;
$C_2H_5COOH$: propionic acid;
$C_3H_7COOH$: butyric acid;
$C_4H_9COOH$: valeric acid;
$C_5H_{11}COOH$: hexanoic (caproic) acid;
$C_6H_{13}COOH$: heptanoic acid;
$C_7H_{15}COOH$: octanoic (caprylic) acid;
$C_8H_{17}COOH$: nonanoic acid;
$C_9H_{19}COOH$: decanoic (capric) acid;
$C_{10}H_{21}COOH$: undecanoic acid;
$C_{11}H_{23}COOH$: lauric acid;
$C_{12}H_{25}COOH$: tridecanoic acid;

$C_{13}H_{27}COOH$: myristic acid;
$C_{14}H_{29}COOH$: pentadecanoic acid;
$C_{15}H_{31}COOH$: palmitic acid;
$C_{16}H_{33}COOH$: heptadecanoic acid;
$C_{17}H_{35}COOH$: stearic acid;
$C_{17}H_{33}COOH$: oleic acid;
$C_{17}H_{31}COOH$: linolic acid;
$C_{17}H_{29}COOH$: linolenic acid;
$C_{18}H_{37}COOH$: nonadecanoic acid;
$C_{19}H_{39}COOH$: icosanoic acid.

The preferred acyl groups are derived from $C_{11}H_{23}COOH$: lauric acid;
$C_{13}H_{27}COOH$: myristic acid;
$C_{15}H_{31}COOH$: palmitic acid;
$C_{17}H_{35}COOH$: stearic acid;
$C_{17}H_{33}COOH$: oleic acid;
$C_{17}H_{31}COOH$: linolic acid;
$C_{17}H_{29}COOH$: linolenic acid;

and particularly palmitic acid.

A straight or branched hydrocarbon chain having 1–4 carbon atoms, is preferably an alkyl group having 1–4 carbon atoms, particularly a methyl group.

A straight or branched hydrocarbon chain having 1–10 carbon atoms is preferably an alkyl group having 1–10 carbon atoms. More preferred is an alkyl group with 1–4 carbon atoms. Particularly preferred is a methyl or a propyl group.

Of the two halogen atoms specified in the definitions of $X_1$ and $X_2$, fluorine is preferred.

The preferred compounds of the invention are those of formula I wherein the 1,2-position is saturated. Also preferred are compounds of formula I wherein $X_1$ and $X_2$ are both fluorine.

Particularly preferred compounds of the invention are those of formula I wherein the 1,2-position is saturated,
$R_1$ is a hydrogen atom,
$R_2$ is a propyl group,
$R_3$ is acyl having 11–20 carbon atoms,
$X_1$ is fluorine and
$X_2$ is fluorine.

Another preferred compound of the invention is the one of the formula I wherein the 1,2-position is a double bond,
$R_1$ is hydrogen,
$R_2$ is propyl,
$R_3$ is palmitoyl,
$X_1$ is fluorine and
$X_2$ is fluorine.

Another preferred compound is (22R)-16α,17α-butylidenedioxy-21-capryloxy-6α,9α-difluoro-11β-hydroxypregn-4-ene-3,20-dione (Example 29)

The most preferred compound of the invention has the formula

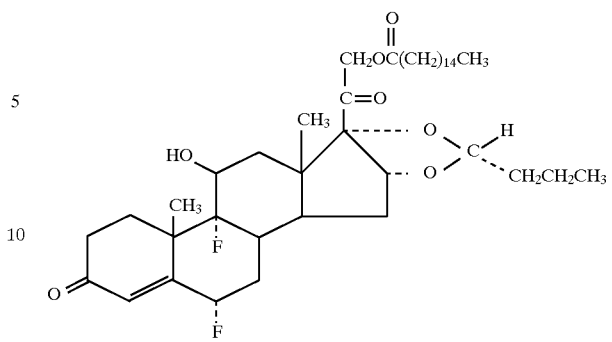

The preferred embodiment of the invention is a composition containing the preferred compound of the invention in combination with liposomes.

Where an object of the invention is to provide a pharmaceutical composition containing liposomes, the active compound of the composition is preferably a compound of formula I wherein $R_3$ is acyl having 11–20 carbon atoms.

Where an object of the invention is to provide a pharmaceutical composition without liposomes, the active compound of the composition is preferably a compound of formula I wherein $R_3$ is acyl having 1–10 carbon atoms, more preferably 5–10 carbon atoms.

The individual stereoisomeric components present in a mixture of a steroid having the above formula (I) can be elucidated in the following way with respect to the chirality at the carbon atom in the 22-position and with respect to the $R_2$ substituent:

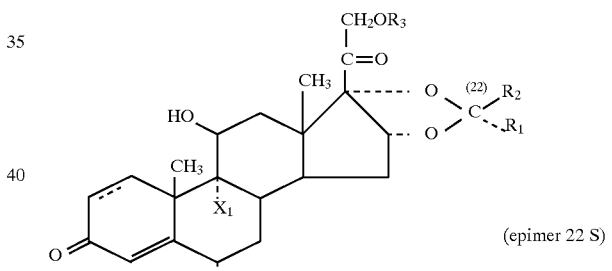

(epimer 22 S)

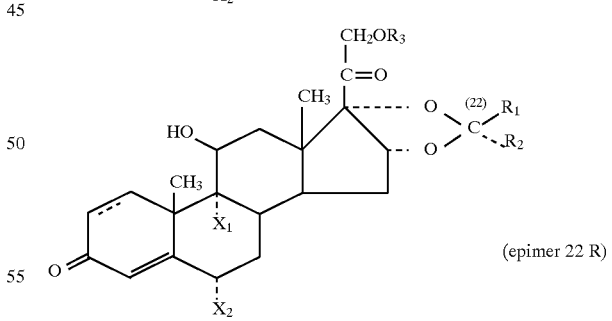

(epimer 22 R)

The preferred stereoisomeric component has the 22R configuration.

Methods of preparation

The steroid esters,

wherein St is

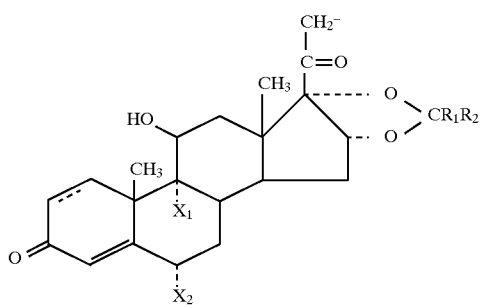

and $X_1$, $X_2$, $R_1$, $R_2$ have the meanings given above; $R_4$ is a straight or branched, saturated or unsaturated alkyl group with 1–19 carbon atoms; and the 1,2-position is saturated or is a double bond, are prepared by any of the following alternative methods.

A. Reaction of a compound of the formula

St—OH wherein St has the definition given above, with a compound of the formula $$R_4COH \;\; (O=)$$

wherein $R_4$ has the definition given above.

The esterification of the 21-hydroxy compound may be effected in a known manner, e.g., by reacting the parent 21-hydroxy steroid with the appropriate carboxylic acid, advantageously in the presence of trifluoroacetic anhydride and preferably in the presence of an acid catalyst, e.g., p-toluenesulfonic acid.

The reaction is advantageously performed in an organic solvent such as benzene or methylene chloride, the reaction being conveniently performed at a temperature of 20+–100° C.

B. Reaction of a compound of the formula

St—OH wherein St has the definition given above, with a compound of the formula $$R_4CX \;\; (O=)$$

wherein $R_4$ has the definition given above and X is a halogen atom, such as chlorine; bromine; iodine and fluorine, or the group $$-O-C(=O)-R_4$$

wherein $R_4$ has the definition given above.

The parent 21-hydroxy compound may be treated with the appropriate carboxylic acid halide or anhydride, preferably in a solvent such as a halogenated hydrocarbon, e.g. methylene chloride, or an ether, e.g. dioxane, in the presence of a base such as triethylamine or pyridine, preferably at low temperature, e.g. −5° C. to +30° C.

C. Reaction of a compound of the formula

St—Y wherein St has the definition given above and Y is selected from halogen, e.g. Cl, Br and I, or from mesylate or p-toluenesulfonate, with a compound of the formula $$R_4CO^{\ominus}A^{\oplus} \;\; (O=)$$

wherein $R_4$ has the definition given above and $A^{\oplus}$ is a cation.

A salt of the appropriate carboxylic acid with an alkali metal, e.g. lithium, sodium or potassium, or a triethyl ammonium or tributylammonium salt, may be reacted with the appropriate alkylating agent of the formula St—Y. The reaction is performed preferably in a polar solvent such as acetone, methylethyl ketone, dimethyl formamide or dimethyl sulfoxide, conveniently at a temperature in the range 25°–100° C.

In any of methods A–C a final reaction step to resolve an epimeric mixture into its components may be necessary in case a pure epimer is desired.

Pharmaceutical preparations

Depending on the site of inflammation, the compounds of the invention may be used in different modes of local administration, e.g. percutaneous, parenteral or for local administration in the respiratory tract by inhalation. An important aim of the formulation design is to reach optimal bioavailability of the active steroid ingredient. For percutaneous formulations this is advantageously achieved if the steroid is dissolved with a high thermodynamic activity in the vehicle. This may be attained by using a suitable system of solvents comprising suitable glycols, such as propylene glycol or 1,3-butanediol either as such or in combination with water.

It is also possible to dissolve the steroid either completely or partially in a lipophilic phase with the aid of a surfactant as a solubilizer. The percutaneous compositions can be ointments, oil in water creams, water in oil creams or lotions. In emulsion vehicles the system comprising the dissolved active component can make up the disperse phase as well as the continuous one. The steroid can also exist in the above compositions as a micronized, solid substance.

Pressurized aerosols for steroids are intended for oral or nasal inhalation. The aerosol system is designed in such a way that each delivered dose contains 10–1000 μg, preferably 20–250 μg of the active steroid. The most active steroids are administered in the lower part of the dose range. The micronized steroid consists of particles substantially smaller than 5 μm, which are suspended in a propellant mixture with the assistance of a dispersant, such as sorbitan trioleate, oleic acid, lecithin or a sodium salt of dioctylsulphosuccinic acid.

The steroid can also be administered by means of a dry powder inhaler.

One option is to mix the micronized steroid with a carrier substance such as lactose or glucose. The powder mixture is dispensed into hard gelatin capsules, each containing the desired dose of the steroid. The capsule is then placed in a powder inhaler and the dose is inhaled into the patient's airways.

Another option is to process the micronized powder into spheres which break up during the dosing procedure This spheronized powder is filled into the drug reservoir in a multidose inhaler, e.g. Turbuhaler™. A dosing unit meters the desired dose which is then inhaled by the patient. With this system the steroid with or without a carrier substance is delivered to the patient.

The steroid can also be included in formulations intended for treating inflammatory bowel diseases, either by the oral route or rectally. Formulations for the oral route should be constructed so that the steroid is delivered to the inflamed parts of the bowel. This can be accomplished by different combinations of enteric and/or slow or control release principles. For the rectal route an enema-type formulation is suitable.

Preparation of liposome compositions

The lecithins used in this invention have fatty acid chains of different lengths and therefore have different phase-transition temperatures. Examples of lecithins used are those derived from egg and soybean as well as synthetic lecithins like dimyristoyl phosphatidylcholine (DMPC), dipalmitoyl phosphatidylcholine (DPPC) and distearoyl phosphatidylcholine (DSPC). By manipulation of the structure of the lecithins, stable carriers with variable biodegradable properties can be formulated. This would enable one to prolong the release of the entrapped steroid ester.

The extent of the interaction of the steroid ester with dipalmitoyl phosphatidylcholine (DPPC) vesicles, for example, is dependent on the ester chain length with increased interaction observed as the chain lengthens.

The inclusion of cholesterol or cholesterol derivatives in liposome formulations has become very common due to its properties in increasing liposome stability.

The initial stages of the preparation of liposomes according to the present invention may conveniently follow procedures described in the literature, i.e., the components are dissolved in a solvent, e.g., ethanol or chloroform, which is then evaporated. The resulting lipid layer is then dispersed in the selected aqueous medium whereafter the solution is either shaken or sonicated. The liposomes of this invention preferably have a diameter of between 0.1 and 10 µm.

In addition to the main liposome-forming lipid(s) which is usually phospholipid, other lipids (e.g. cholesterol or cholesterol stearate) in the amount of 0–40% w/w of the total lipids may be included to modify the structure of the liposome membrane. In optimizing the uptake of the liposome a third component providing a negative charge (e.g. dipalmitoyl phosphatidyl glycerol) or a positive charge (e.g. stearylamine acetate or cetylpyridinium chloride) may be incorporated.

A wide range of relative proportions of steroid ester and lipid may be used depending on the lipid and the conditions used. Drying (freeze-drying or spray-drying) of the liposomes in the presence of lactose can be used with a lactose content in the range of 0 to 95% of the final composition.

The particularly preferred composition according to the invention contains liposomes and (22R)-16α,17α-butylidenedioxy-6α,9α-difluoro-11β-hydroxy-21-palmitoyloxypregn-4-ene-3,20-dione. The routes of administration involve powder aerosols, instillation, nebulization and pressurized aerosols.

WORKING EXAMPLES

The invention will be further illustrated by the following nonlimitative examples. In the examples a flowrate of 2.5 ml/cm²/h is used in the preparative chromatographic runs. Molecular weights are in all examples determined with chemical ionization mass spectrometry (CH$_4$ as reagent gas) and the melting points on a Leitz Wetzlar hot stage microscope. The HPLC (High Performance Liquid Chromatography) analyses were performed on a µBondapak C$_{18}$ column (300×3.9 mm i.d.) with a flow rate of 1.0 ml/min and with ethanol/water in ratios between 40:60 and 60:40 as mobile phase, if not otherwise stated.

Example 1

(22R)-16α,17α-Butylidenedioxy-6α,9α-difluoro-11β-hydroxy-21-palmitoyloxypregn-4-ene-3,20-dione A solution of palmitoyl chloride (1.2 g) in 10 ml of dioxane was added dropwise to a solution of (22R)-16α,17α-butylidenedioxy-6α,9α-difluoro-11β,21-dihydroxypregn-4-ene-3,20-dione (200 mg) in 25 ml of pyridine. The reaction mixture was stirred for 16 h at room temperature. Methylene chloride (150 ml) was added and the solution washed with 1M hydrochloric acid, 5% aqueous potassium carbonate and water and dried. The crude product after evaporation was purified by chromatography on a Sephadex LH-20 column (87×2.5 cm) using chloroform as mobile phase. The fraction 210–255 ml was collected and evaporated, leaving 203 mg of (22R)-16α,17α-butylidenedioxy-6α,9α-difluoro-11β-hydroxy-21-palmitoyloxypregn-4-ene-3,20-dione. Melting point 87°–90° C.; molecular weight 706 (calc. 707.0). Purity: 96% (HPLC-analysis).

Example 2

(22R)-16α,17α-Butylidenedioxy-6α,9α-difluoro-11β-hydroxy-21-palmitoyloxypregn-4-ene-3,20-dione To a solution of (22R)-16α,17α-butylidenedioxy-6α,9α-difluoro-11β, 21-dihydroxypregn-4-ene-3,20-dione (50 mg) and palmitoyl chloride (35 mg) in 10 ml of methylene chloride was added dropwise a solution of triethylamine (13 mg) in 2 ml of methylene chloride. The reaction mixture was stirred for 2 h at room temperature. Another 50 ml of methylene chloride was added and the reaction mixture was worked up as in Example 1. The crude product was purified on a Sephadex LH-20 column (85×2.5 cm) using chloroform as mobile phase. The fraction 210–250 ml was collected and evaporated, yielding 34 mg of (22R)-16α,17α-butylidenedioxy-6α,9α-difluoro-11β-hydroxy-21-palmitoyloxypregn-4-ene-3,20-dione. Molecular weight 706 (calc. 707.0). Purity: 95% (HPLC-analysis).

Example 3

(22S)-16α,17α-Butylidenedioxy-6α,9α-difluoro-11β-hydroxy-21-palmitoyloxypregn-4-ene-3,20-dione A solution of palmitoyl chloride (0.4 ml) in 10 ml of dioxane was added dropwise to a solution of (22S)-16α,17α-butylidenedioxy-6α,9α-difluoro-11β,21-dihydroxypregn-4-ene-3,20-dione (70 mg) in 25 ml of pyridine. The reaction mixture was stirred for 16 h at room temperature and worked up as in Example 1. The crude product was purified on a Sephadex LH-20 column (87×2.5 cm) using chloroform as mobile phase. The fraction 225–265 ml was collected and evaporated, yielding 92 mg of (22S)-16α,17α-butylidenedioxy-6α,9α-difluoro-11β-hydroxy-21-palmitoyloxypregn-4-ene-3,20-dione as an oil. Molecular weight: 706 (calc. 707.0). Purity: 97% (HPLC-analysis).

Example 4

(22R)-16α,17α-Butylidenedioxy-6α,9α-difluoro-11β-hydroxy-21-myristoyloxypregn-4-ene-3,20-dione Myristoyl chloride was synthesized by refluxing myristic acid (7.0 g) and thionyl chloride (9 ml) in trichloroethylene (100 ml) for 3 h. The solvent was then evaporated.

To a solution of (22R)-16α,17α-butylidenedioxy-6α,9α-difluoro-11β,21-dihydroxypregn-4-ene-3,20-dione (51 mg) in 10 ml of methylene chloride was added myristoyl chloride (32 mg) followed by triethylamine (13 mg) dissolved in methylene chloride (5 ml). The reaction mixture was stirred for 4 h at room temperature. Further methylene chloride was added and the mixture successively washed with 0.1M hydrochloric acid and water (3×50 ml). After drying and evaporation the residue was purified by chromatography on Merck Kieselgel 60 using heptane:acetone, 6:4, as mobile phase, yielding 27 mg of (22R)-16α,17α-butylidenedioxy-6α, 9α-difluoro-11β-hydroxy-21-myristoyloxypregn-4-ene-3,20-dione. Molecular weight 678 (calc. 678.9). Purity: 96.8% (HPLC-analysis).

Example 5

(22R)-16α,17α-Butylidenedioxy-6α,9α-difluoro-11β-hydroxy-21-lauroyloxypregn-4-ene-3,20-dione To a solution of (22R)-16α,17α-butylidenedioxy-6α,9α-difluoro-11β,21-dihydroxypregn-4-ene-3,20-dione (51 mg) in 5 ml of methylene chloride was added lauroyl chloride (28 mg) followed by triethylamine (13 mg) dissolved in 2 ml of methylene chloride. The reaction mixture was stirred at room temperature for 3 h, further methylene chloride was added and the organic phase washed successively with 0.1M hydrochloric acid and water (3×30 ml). After drying and evaporation the residue was purified by chromatography on Merck Kieselgel 60 using hexane:acetone, 6:4, as mobile phase. The product obtained was further purified in a second chromatographic step using petroleum ether:ethyl acetate, 3:2, as mobile phase yielding 33 mg of (22R)-16α,17α-butylidenedioxy-6α,9α-difluoro-11β-hydroxy-21-lauroyloxypregn-4-ene-3,20-dione. Molecular weight 650 (calc. 650.8). Purity: 96.9% (HPLC-analysis).

Example 6

(22R)-16α,17α-Butylidenedioxy-6α,9α-difluoro-11β-hydroxy-21-palmitoyloxypregna-1,4-diene-3,20-dione A solution of palmitoyl chloride (2.3 ml) in 15 ml of dioxane was added dropwise to a solution of (22R)-16α,17α-butylidenedioxy-6α,9α-difluoro-11β,21-dihydroxypregna-1,4-diene-3,20-dione (700 mg) in 30 ml of pyridine. The reaction mixture was stirred at room temperature overnight and worked up as in Example 1. The crude product was purified on a Sephadex LH-20 column (76×6.3 cm) using heptane: chloroform:ethanol, 20:20:1, as mobile phase. The fraction 1020–1350 ml was collected and evaporated, yielding 752 mg of (22R)-16α,17α-butylidenedioxy-6α,9α-difluoro-11β-hydroxy-21-palmitoyloxypregna-1,4-diene-3,20-dione. Melting point 141°–145° C.; $[\alpha]_D^{25}$=+71.6° (c=0.204; $CH_2Cl_2$); molecular weight 704 (calc. 704.9). Purity: 97.7% (HPLC-analysis).

Example 7

(22S)-16α,17α-Butylidenedioxy-6α,9α-difluoro-11β-hydroxy-21-palmitoyloxypregna-1,4-diene-3,20-dione A solution of palmitoyl chloride (0.5 ml) in 5 ml of dioxane was added dropwise to a solution of (22S)-16α,17α-butylidenedioxy-6α,9α-difluoro-11β,21-dihydroxypregna-1,4-diene-3,20-dione (150 mg) in 10 ml of pyridine. The reaction mixture was stirred at room temperature overnight and worked up as in Example 1. The crude product was purified on a Sephadex LH-20 column (89×2.5 cm) using heptane: chloroform:ethanol, 20:20:1, as mobile phase. The fraction 215–315 ml was collected and evaporated, yielding 132 mg of (22S)-16α,17α-butylidenedioxy-6α,9α-difluoro-11β-hydroxy-21-palmitoyloxypregna-1,4-diene-3,20-dione. Melting point 176°–180° C.; $[\alpha]_D^{25}$=+47.50 (c=0.198; $CH_2Cl_2$); molecular weight 704 (calc. 704.9). Purity: 99% (HPLC-analysis).

Example 8

(22R)-21-Acetoxy-16α,17α-butylidenedioxy-6α,9α-difluoro-11β-hydroxypregn-4-ene-3,20-dione A solution of acetyl chloride (38 mg) in 5 ml of dioxane was added dropwise to a solution of (22R)-16α,17α-butylidenedioxy-6α,9α-difluoro-11β,21-dihydroxypregn-4-ene-3,20-dione (75 mg) in 5 ml of pyridine. The reaction mixture was stirred for 16h at room temperature. After evaporation methylene chloride (75 ml) was added, and the solution was washed with cold 5% aqueous potassium carbonate and saturated sodium chloride solution. The crude product after evaporation was purified by chromatography on a Sephadex LH-20 column (85×2.5 cm) using chloroform as the mobile phase. The fraction 365–420 ml was collected and evaporated, leaving 57 mg of (22R)-21-acetoxy-16α,17α-butylidenedioxy- 6α,9α-difluoro-11β-hydroxypregn-4-ene-3,20-dione. Melting point 182°–189°; $[\alpha]_D^{25}$+112.0° (c=0.225; $CH_2Cl_2$); molecular weight 510 (calc 510.6). Purity 99.0% (HPLC-analysis).

Example 9

(22R)-16α,17α-Butylidenedioxy-6α,9α-difluoro-11β-hydroxy-21-valeroyloxypregn-4-ene-3,20-dione A solution of valeroyl chloride (60 mg) in 5 ml of dioxane was added dropwise to a solution of (22R)-16α,17α-butylidenedioxy-6α,9α-difluoro-11β,21-dihydroxypregn-4-ene-3,20-dione (75 mg) in 5 ml of pyridine. The reaction mixture was stirred for 16h at room temperature. After evaporation methylene chloride (75 ml) was added, and the solution was washed with cold 5% aqueous potassium carbonate and saturated sodium chloride solution. The crude product after evaporation was purified by chromatography on a Sephadex LH-20 column (85×2.5 cm) using chloroform as the mobile phase. The fraction 265–325 ml was collected and evaporated, leaving 50 mg of (22R)-16α,17α-butylidenedioxy-6α,9α-difluoro-11β-hydroxy-21-valeroyloxypregn-4-ene-3,20-dione. Melting point 181°–185°; $[\alpha]_D^{25}$=+109.4° (c=0.212; $CH_2Cl_2$); molecular weight 552 (calc. 552.7). Purity 99.8% (HPLC-analysis).

Example 10

(22R)-16α,17α-Butylidenedioxy-6α,9α-difluoro-11β-hydroxy-21-capryloxypregna-1,4-diene-3,20-dione A solution of decanoyl chloride (0.2 ml) in 3 ml of dioxane was added dropwise to a solution of (22R)-16α,17α-butylidenedioxy-6α,9α-difluoro-11β,21-dihydroxypregna-1,4-diene-3,20-dione (100 mg) in 6 ml of pyridine. The reaction mixture was stirred at room temperature overnight and worked up as in Example 1. The crude product was purified on a Sephadex LH-20 column (71×6.3 cm) using chloroform as mobile phase. The fraction 1470–1725 ml was collected and evaporated, yielding 113 mg of (22R)-16α,17α-butylidenedioxy-6α,9α-difluoro-11β-hydroxy-21-capryloxypregna-1,4-diene-3,20-dione. Melting point 182–°184° C. $[\alpha]_D^{25}$=+71.5° (c=0.186; $CH_2Cl_2$). Molecular weight 620 (calc. 620.9). Purity: 97.7% (HPLC-analysis).

Example 11

6α,9α-Difluoro-11β,21-dihydroxy-16α,17α-[(1-methylethylidene)bis(oxy)]pregn-4-ene-3,20-dione A suspension of 0.9 g of tris(triphenylphosphine)rhodium chloride in 250 ml of degassed toluene was hydrogenated for 45 min at room temperature and atmospheric pressure. A solution of 1.0 g of fluocinolone 16α,17α-acetonide in 100 ml of absolute ethanol was added and the hydrogenation was continued for another 40 h. The reaction product was evaporated and the residue purified by flash chromatography on silica using acetone-petroleum ether as mobile phase to remove the main part of the catalyst. The eluate was evaporated and the residue further purified by chromatography on a Sephadex LH-20 column (72.5×6.3 cm) using chloroform as mobile phase. The fraction 3555–4125 ml was collected and evaporated, yielding 0.61 g of 6α,9α-difluoro-11β,21-dihydroxy-16α,17α-[((1-methylethylidene)-bis(oxy)]pregn-4-ene-3,20-dione. Melting point 146°–151° C. $[\alpha]_D^{25}$=+124.5° (c=0.220;$CH_2Cl_2$). Molecular weight 454 (calc. 454.6). purity: 98.5% (HPLC-analysis).

Example 12

6α,9α-Difluoro-11β-hydroxy-16α,17α-[(1methylethylidene)bis(oxy)]21-palmitoyloxypregn-4-ene3,20-dione A solution of palmitoyl chloride (2.1 ml) in 15 ml of dioxane was added dropwise to a solution of 6α,9α-difluoro-11β,21-dihydroxy-16α,17α-[(1-methyl-ethylidene) bis (oxy)]pregn-4-ene-3,20-dione (310 mg) in 30 ml of pyridine. The reaction mixture was stirred at room temperature overnight and worked up as in Example 1. The crude product was purified on a Sephadex LH-20 column (76×6.3 cm) using heptane:chloroform:ethanol, 20:20:1, as mobile phase. The fraction 1035–1260 ml was collected and evaporated, yielding 158 mg of 6α,9α-difluoro-116-hydroxy-16α,17α[(1-methylethylidene)bis(oxy)]-21-palmitoyloxypregn-4-ene-3,20-dione. Melting point 82°–86° C. $[\alpha]_D^{25}$=+85.3° (c=0.232; $CH_2Cl_2$). Molecular weight 692 (calc. 692.9). Purity: 98.6% (HPLC-analysis).

Example 13

(22R)- and (22S)-21-Acetoxy-16α-17α-butylidenedioxy-6α-fluoro-11β-hydroxypregn-4-ene-3,20-dione (22RS)-16α,17α-Butylidenedioxy-6α-fluoro-11β,21-dihydroxypregn-4-ene-3,20-dione (68 mg) was dissolved in 1 ml of pyridine. Acetic anhydride (1 ml) was added and the reaction mixture stirred at room temperature for 1 h, poured into ice water and extracted with 3×25 ml of methylene chloride. The extract was dried and evaporated. The residual 22RS-mixture was resolved by chromatography on a Sephadex LH-20 column (89×2.5 cm) using heptane:chloroform:ethanol, 20:20:1, as mobile phase. The fractions 380–400 ml (A) and 420–440 ml (B) were collected and evaporated.

After precipitation from methylene chloride-petroleum ether, fraction A yielded 14 mg of (22S)-21-acetoxy-16α,17α-butylidenedioxy-6α-fluoro-11β-hydroxypregn-4-ene-3,20-dione. Melting point 179°–186° C. $[\alpha]_D^{25}$=+86.2° (c=0.188; $CH_2Cl_2$). Molecular weight 492 (calc. 492.6). Purity: 97.5% (HPLC-analysis).

Fraction B gave after precipitation 20 mg of (22R)-21acetoxy-16α,17α-butylidenedioxy-6α-fluoro-11β-hydroxypregn-4-ene-3,20-dione. Melting point 169°–172° C. $[\alpha]_D^{25}$=+139.0° (C=0.200; $CH_2Cl_2$). Molecular weight 492 (calc. 492.6). Purity: 97.9% (HPLC-analysis).

Example 14

(22RS)-16α,17α-Butylidenedioxy-6α-fluoro-11β-hydroxy-21-palmitoyloxypregn-4-ene-3,20-dione To a suspension of 1.4 g of tris(triphenylphosphine)-rhodium chloride in 300 ml of toluene was added a solution of 1170 mg of 6α-fluoro-11β,16α,17α,21-tetrahydroxypregna-1,4-diene-3,20-dione in 250 ml of absolute ethanol. The mixture was hydrogenated 22 h at room temperature and atmospheric pressure and evaporated. The residue was precipitated from acetone-chloroform, yielding 661 mg of 6α-fluoro-11β,16α,17α,21-tetrahydroxypregn-4-ene-3,20-dione. Molecular weight 396 (calc. 396.5). Purity: 96.6% (HPLC-analysis).

6α-Fluoro-11β,16α,17α,21-tetrahydroxypregn-4-ene-3,20-dione (308 mg) was added in portions to a solution of butanal (115 mg) and 70% perchloric acid (0.2 ml) in 50 ml of dioxane. The reaction mixture was stirred at room temperature for 6 h. Methylene chloride (200 ml) was added and the solution washed with 10% aqueous potassium carbonate and water and dried. The residue after evaporation was purified on a Sephadex LH-20 column (87×2.5 cm) using chloroform as mobile phase. The fraction 420–500 ml was collected and evaporated, yielding 248 mg of (22RS)-16α,17α-butylidenedioxy-6α-fluoro-11β,21-dihydroxypregn-4-ene-3,20-dione. Melting point 85°–96° C. $[\alpha]_D^{25}$=+119.8° (c=0.192; $CH_2Cl_2$). Molecular weight 450 (calc. 450.6). Purity: 96.1% (HPLC-analysis). The distribution between the 22R- and 22S-epimers was 59/41 (HPLC-analysis).

A solution of palmitoyl chloride (0.21 ml) in 3 ml of dioxane was added dropwise to a solution of (22RS)-16α,17α-butylidenedioxy-6α-fluoro-11β,21-dihydroxypregn-4-ene-3,20-dione (50 mg) in 6 ml of pyridine. The reaction mixture was stirred at room temperature overnight and worked up as in Example 1. The crude product was purified on a Sephadex LH-20 column (89×2. 5 cm) using heptane:chloroform: ethanol, 20:20:1, as mobile phase. The fraction 185–230 ml was collected and evaporated, yielding 42 mg of (22RS)-16α,17α-butylidenedioxy-6α-fluoro-11β-hydroxy-21-palmitoyloxypregn-4-ene-3,20-dione as an oil. Molecular weight 688 (calc. 688.97). Purity: 99.0%. The distribution between the 22R- and 22S-epimers was 15/85 (HPLC-analysis).

Example 15

(22RS)-16α,17α-Butylidenedioxy-6α-fluoro-11β-hydroxy-21-palmitoyloxypregn-4-ene-3,20-dione (22RS)-16α,17α-Butylidenedioxy-6α-fluoro-11β,21-diydroxypregn-4-ene-3,20-dione (225 mg) was resolved by preparative HPLC in portions on a μBondapak $C_{18}$, column (150×19 mm) using ethanol:water, 40:60, as mobile phase. The fractions centered at 265 ml (A) and 310 ml (B) were collected and evaporated. After precipitation from methylene chloride-petroleum ether, fraction A yielded 68 mg of (22R)-16α,17α-butylidenedioxy-6α-fluoro-11β,21-dihydroxypregn-4-ene-3,20-dione. Melting point 180°–192° C. $[\alpha]_D^{25}$=+138.9° (c=0.144; $CH_2Cl_2$). Molecular weight 450 (calc. 450.6). Purity: 99.4% (HPLC-analysis).

Fraction B gave after precipitation 62 mg of (22S)-16α,17α-butylidenedioxy-6α-fluoro-11β,21-dihydroxypregn-4-ene-3,20-dione. Melting point 168°–175° C. $[\alpha]_D^{25}$=+

103.7° (c=0.216; $CH_2Cl_2$). Molecular weight 450 (calc. 450.6). Purity: 99.5% (HPLC-analysis).

A solution of palmitoyl chloride (0. 22 ml) in 5 ml of dioxane was added dropwise to a solution of (22R)-16α,17α-butylidenedioxy-6α-fluoro-11β,21-dihydroxypregn-4-ene-3,20-dione (32 mg) in 10 ml of pyridine. The reaction mixture was stirred at room temperature overnight and worked up as in Example 1. The crude product was purified on a Sephadex LH-20 column (87×2.5 cm) using chloroform as mobile phase. The fraction 215–250 ml was collected and evaporated, yielding 38 mg of (22R)-16α,17α-butylidenedioxy-6α-fluoro-11β-hydroxy-21-palmitoyloxypregn-4-ene-3,20-dione as an oil. Molecular weight 688 (calc. 688.97). Purity: 96.0% (HPLC-analysis)

Example 16

(22S)-16α,17α-Butylidenedioxy-6α-fluoro-11β-hydroxy-21-palmitoyloxypregn-4-ene-3,20-dione (22RS)-16α,17α-Butylidenedioxy-6α-fluoro-11β,21-dihydroxypregn-4-ene-3,20-dione (68 mg) was dissolved in 1 ml of pyridine. Acetic anhydride (1 ml) was added and the reaction mixture stirred at room temperature for 1 h, poured into ice water and extracted with 3×25 ml of methylene chloride. The extract was dried and evaporated. The residual 22RS epimeric mixture was resolved by chromatography on a Sephadex LH-20 column (89×2.5 cm) using heptane:chloroform:ethanol, 20:20:1, as mobile phase. The fractions 380–400 ml (A) and 420–440 ml (B) were collected and evaporated.

After precipitation from methylene chloride-petroleum ether, fraction A yielded 14 mg of (22S)-21-acetoxy-16α,17α-butylidenedioxy-6α-fluoro-11β-hydroxypregn-4-ene-3,20-dione. Melting point 179°–186° C. $[\alpha]_D^{25}$=+86.2° (c=0.188; $CH_2Cl_2$). Molecular weight 492 (calc. 492.6). Purity: 97.5% (HPLC-analysis).

Fraction B gave after precipitation 20 mg of (22R)-21acetoxy-16α,17α-butylidenedioxy-6α-fluoro-11β-hydroxypregn-4-ene-3,20-dione. Melting point 169°–172° C. $[\alpha]_D^{25}$=+139.0° (c=0.200; $CH_2Cl_2$). Molecular weight 492 (calc. 492.6). Purity: 97.9% (HPLC-analysis).

To a solution of 14 mg of (22S)-21-acetoxy-16α,17αbutylidenedioxy-6α-fluoro-11β-hydroxypregn-4-ene-3,20-dione in 2 ml of ethanol, 2 ml of 2M hydrochloric acid was added. After stirring at 60° C. for 5 h the reaction mixture was neutralized with saturated aqueous sodium hydrogen carbonate and extracted with 3×25 ml of methylene chloride. The combined extracts were washed with water, dried and evaporated. The residue was purified on a Sephadex LH-20 column (87×2.5 cm) using chloroform as mobile phase. The fraction 455–510 ml was collected and evaporated, giving 7 mg of (22S)-16α,17α-butylidenedioxy-6α-fluoro-11β,21-dihydroxypregn-4-ene-3,20-dione. Molecular weight 450 (calc. 450.6). Purity: 96.6%.

A solution of palmitoyl chloride (195 mg) in 5 ml of dioxane was added dropwise to a solution of (22S)-16α,17αbutylidenedioxy-6α-fluoro-11β,21-dihydroxypregn-4-ene-3,20-dione (32 mg) in 10 ml of pyridine. The reaction mixture was stirred at room temperature overnight and worked up as in Example 1. The crude product was purified on a Sephadex LH-20 column (89×2.5 cm) using heptane:chloroform,:ethanol, 20:20:1, as mobile phase. The fraction 205–245 ml was collected and evaporated, yielding 37 mg of (22S)-16α,17α-butylidenedioxy-6α-fluoro-11β-hydroxy-21-palmitoyloxypregn-4-ene-3,20-dione as an oil. Molecular weight 688 (calc. 688.97). Purity: 96.4% (HPLC-analysis).

Example 17

(22RS)-16α,17α-Butylidenedioxy-6α-fluoro-11β-hydroxy-21-lauroyloxypregn-4-ene-3,20-dione A solution of lauroyl chloride (0.4 ml) in 3 ml of dioxane was added dropwise to a solution of (22RS)-(16α,17α)-butylidenedioxy-6α-fluoro-11β,21-dihydroxypregn-4-ene-3,20-dione (50 mg) in 6 ml of pyridine. The reaction mixture was stirred at room temperature overnight and worked up as in Example 1. The crude product was purified on a Sephadex LH-20 column (89×2.5 using heptane:chloroform:ethanol, 20:20:1, as mobile phase. The fraction 215–250 ml was collected and evaporated, yielding 15 mg of (22RS)-16α,17α-butylidenedioxy-6α-fluoro-11β-hydroxy-21-lauroyloxypregn-4-ene-3,20-dione. Melting point 125°–143° C. $[\alpha]_D^{25}$=+92.8° (c=0.208; $CH_2Cl_2$). Molecular weight 632 (calc. 632.9). Purity: 96.2% (HPLC-analysis). The distribution between the 22R- and 22S-epimers was 58/42 (HPLC-analysis).

Example 18

(22R)-16α,17α-Butylidenedioxy-6α-fluoro-11β-hydroxy-21-palmitoyloxypregna-1,4-diene-3,20-dione 6α-Fluoro-11β,16α,17α,21-tetrahydroxypregna-1,4-diene-3,20-dione (400 mg) was added in portions to a solution of butanal (0.18 ml) and 70% perchloric acid (0.2 ml) in 50 ml of dioxane. The reaction mixture was stirred at room temperature for 16 h. Methylene chloride (200 ml) was added and the solution washed with 10% aqueous potassium carbonate and water and dried. The residue after evaporation was purified on a Sephadex LH-20 column (75×6.3 cm) using chloroform as mobile phase. The fraction 2880–3300 ml was collected and evaporated, yielding 1209 mg of (22RS)-16α,17α-butylidenedioxy-6α-fluoro-11β,21-dihydroxypregna-1,4-diene-3,20-dione. Molecular weight 448 (calc. 448.5). The purity was 95.7% and the distribution between the 22R- and 22S-epimers 55/45 (HPLC-analysis).

(22RS)-16α,17α-Butylidenedioxy-6α-fluoro-11β,21-dihydroxypregna-1,4-diene-3,20-dione (36 mg) was chromatographed on a Sephadex LH-20 column (89×2.5 cm) using heptane:chloroform:ethanol, 20:20:1, as mobile phase. The fractions 1720–1800 ml (A) and 1960–2025 ml (B) were collected and evaporated. The two products were precipitated from methylene chloride-petroleum ether. The product from fraction A (12 mg) was identified with $^1$H-NMR and mass spectrometry to be (22S)-16α,17α-butylidenedioxy-6α-fluoro-11β,21-dihydroxypregna-1,4-diene-3,20-dione and the product from the B fraction (10 mg) as the 22R-epimer.

The epimers had the following properties. Epimer 22S: Melting point 172°–180° C.; $[\alpha]_D^{25}$=+62.3° (c=0.132; $CH_2Cl_2$); molecular weight 448 (calc. 448.5). Epimer 22R: Melting point 95°–106° C.; $[\alpha]_D^{25}$=+105.9° (c=0.152; $CH_2Cl_2$); molecular weight 448 (calc. 448.5). The purity of the epimers was determined by HPLC-analysis to be 98.9% for the 22S-epimer and 97.7% for the 22R-epimer.

A solution of palmitoyl chloride (172 mg) in 5 ml of dioxane was added dropwise to a solution of (22R)-16α, 17abutylidenedioxy-6α-fluoro-11β, 21-dihydroxypregna-1,4-diene-3,20-dione (56 mg) in 10 ml of pyridine. The reaction mixture was stirred at room temperature overnight and worked up as in Example 1. The crude product was purified on a Sephadex LH-20 column (89×2.5 cm) using heptane: chloroform: ethanol, 20:20:1, as mobile phase. The fraction 225–285 ml was collected and evaporated, yielding 31 mg of (22R)-16α,17α-butylidenedioxy-6α-fluoro-11β-hydroxy-21-palmitoyloxypregna-1,4-diene-3,20-dione. Melting point 95°–100° C. $[\alpha]_D^{25}$=+68.0° (c=0.200; $CH_2Cl_2$). Molecular weight 686 (calc. 686.95). Purity: 97.7% (HPLC-analysis).

Example 19

(22S)-16α,17α-Butylidenedioxy-6α-fluoro-11β-hydroxy-21-palmitoyloxypregna-1,4-diene-3,20-dione A solution of palmitoyl chloride (110 mg) in 5 ml of dioxane was added dropwise to a solution of (22S)-16α,17abutylidenedioxy-6α-fluoro-11β,21-dihydroxypregna-1,4-diene-3,20-dione (46 mg) in 10 ml of pyridine. The reaction mixture was stirred at room temperature overnight and worked up as in Example 1. The crude product was purified on a Sephadex LH-20 column (89×2.5 cm) using heptane: chloroform:ethanol, 20:20:1, as mobile phase. The fraction 185–225 ml was collected and evaporated, yielding 37 mg of (22S)-16α,17α-butylidenedioxy-6α-fluoro-11β-hydroxy-21-palmitoyloxypregna-1,4-diene-3,20-dione.

Melting point 65°–68° C. $[\alpha]_D^{25}$=+53.0° (c=0.200; $CH_2Cl_2$). Molecular weight 686 (calc. 686.95). Purity: 95.9% (HPLC-analysis).

Example 20

6α-Fluoro-11β,21-dihydroxy-16α,17α-[(1methylethylidene)bis(oxy)]pregn-4-ene-3,20-dione A suspension of 2.1 g of tris(triphenylphosphine)rhodium chloride in 500 ml of toluene was hydrogenated at room temperature and atmospheric pressure for 45 min, when the catalyst was in solution. A solution of 2.0 g of 6α-fluoro-11β,21-dihydroxy- 16α,17α-[(1-methylethylidene)bis(oxy)]pregna-1,4-diene-3,20-dione in 1000 ml of absolute ethanol was added and the hydrogenation was continued for another 65 h. The reaction mixture was evaporated and the residue purified on a Sephadex LH-20 column (71×6.3 cm) using chloroform as mobile phase. The fraction 2010–2445 ml was collected and evaporated, yielding 1.51 g of 6αfluoro-11β,21-dihydroxy-16α,17α-[(1-methylethylidene)bis(oxy)]pregn-4-ene-3,20-dione. Melting point 209°–219° C. $[\alpha]_D^{25}$=+133.5° (c=0.230; $CH_2Cl_2$). Molecular weight 436 (calc. 436.5). Purity: 99.6% (HPLC-analysis).

Example 21

6α-Fluoro-11β-hydroxy-16α,17α-[(1-methylethylidene)bis(oxy)]-21-palmitoyloxypregn-4-ene-3 20-dione A solution of palmitoyl chloride (0.21 ml) in 3 ml of dioxane was added dropwise to a solution of 6α-fluoro11β,21-dihydroxy-16α,17α-[(1-methylethylidene)bis(oxy)] pregn-4-ene-3,20-dione in 6 ml of pyridine. The reaction mixture was stirred at room temperature overnight and worked up as in Example 1. The crude product was purified on a Sephadex LH-20 column (76×6.3 cm) using heptane: chloroform:ethanol, 20:20:1, as mobile phase. The fraction 1035–1230 ml was collected and evaporated, yielding 63 Mg of 6α-fluoro-11β-hydroxy-16α,17α-[(1-methylethylidene)bis(oxy)]-21-palmitoyloxypregn-4-ene-3,20-dione. Melting point 99°–101° C. $[\alpha]_D^{25}$=+89.8° (c=0.206; $CH_2Cl_2$)). Molecular weight 674 (calc. 674.94). Purity: 97.9% (HPLC-analysis).

Example 22

9α-Fluoro-11β,21-dihydroxy-16α,17α-[(1-methylethylidene)bis(oxy)]pregn-4-ene-3,20-dione A solution of 675 mg of tris(triphenylphosphine)rhodium chloride in 250 ml of toluene was hydrogenated at room temperature and atmospheric pressure for 45 min. A solution of 1 g of triamcinolone 16α,17α-acetonide in 100 ml of absolute ethanol was added and the hydrogenation was continued for another 40 h. The reaction mixture was evapo-rated and the main part of the catalyst removed by flash chromatography with acetone:petroleum ether (b.p. 40°–60° C.), 40:60, as mobile phase. The crude product was further purified on a Sephadex LH-20 column (72.5×6.3 cm) using chloroform as mobile phase. The fraction 2746–3195 ml was collected and evaporated, yielding 404 mg of 9α-fluoro-11β,21-dihydroxy-16α,17α-[(1-methylethylidene)-bis(oxy)]pregn-4-ene-3,20-dione. Melting point 238°–41° C. $[\alpha]_D^{25}$=+145.2° (c=0.288; $CH_2Cl_2$)). Molecular weight 436 (calc. 436.5). Purity: 99% (HPLC-analysis).

Example 23

9α-Fluoro-11β-hydroxy-16α,17α[(1-methylethylidene)bis(oxy)]-21-palmitoyloxypregn-4-ene-3,20-dione A solution of palmitoyl chloride (0–69 ml) in 10 ml of dioxane was added dropwise to a solution of 9α-fluoro11β,21-dihydroxy-16α,17α-[(1-methylethylidene)-bis(oxy)] pregn-4-ene-3,20-dione in 20 ml of pyridine. The reaction mixture was stirred at room temperature overnight and worked up as in Example 1. The crude product was purified on a Sephadex LH-20 column (89×2.5 cm) using heptane:chloroform:ethanol, 20:20:1, as mobile phase. The fraction 240–305 ml was collected and evaporated, yielding 102 mg of 6α-fluoro-11β-hydroxy-16α,17α-[(1-methylethylidene)bis(oxy)]-21-palmitoyloxypregn-4-ene-3,20-dione as an oil. Molecular weight 674 (calc. 674.94). Purity: 98% (HPLC-analysis).

Example 24

(22RS)-16α,17α-Butylidenedioxy-9α-fluoro-11β-hydroxy-21-palmitoyloxypregn-4-ene-3,20-dione To a solution of freshly distilled butanal (100 mg) and 0.2 ml of perchloric acid (70%) in 50 ml of purified and dried dioxane, 9α-fluoro-11β,16α,17α,21-tetrahydroxypregn-4-ene-3,20-dione (340 mg) was added in small portions with stirring during 20 min. The reaction mixture was stirred at room temperature for another 5 h. Methylene chloride (200 ml) was added, and the solution was washed with aqueous potassium carbonate and water and dried over anhydrous magnesium sulfate. The crude product obtained after evaporation was purified on a Sephadex LH-20 column (72.5×6.3 cm) using chloroform as mobile phase. The fraction 2760–3195 ml was collected and evaporated, yielding 215 mg of (22RS)-16α,17α-butylidenedioxy-9α-fluoro-11β,21-dihydroxypregn-4-ene-3,20-dione. Molecular weight 450 (calc. 450.6). Purity: 97.4% (HPLC-analysis).

A solution of palmitoyl chloride (0.13 ml) in 2.5 ml of dioxane was added dropwise to a solution of (22RS)-16α,17α-butylidenedioxy-9α-fluoro-11β,21-dihydroxypregn-4-ene-3,20-dione (40 mg) in 5 ml of pyridine. The reaction mixture was stirred at room temperature overnight and worked up as in Example 1. The crude product was purified on a Sephadex LH-20 column (87×2.5 cm) using chloroform as mobile phase. The fraction 220–300 ml was collected and evaporated, yielding 42 mg of (22RS)-16α,17α-butylidenedioxy-9α-fluoro-11β-hydroxy-21-palmitoyloxypregn-4-ene-3,20-dione as an oil. Molecular weight 688 (calc. 688.97). The distribution between the 22R- and 22S-epimers was 61/39 (HPLC-analysis).

Example 25

(22R)-16α,17α-Butylidenedioxy-9α-fluoro-11β-hydroxy-21-palmitoyloxypregn-4-ene-3,20-dione (22RS)-16α,17α-Butylidenedioxy-9α-fluoro-22β,21-dihydroxypregn-4-ene-3,20-dione (200 mg) was resolved by chromatography on a Sephadex LH-20 column (76×6.3 cm) using a heptane:chloroform:ethanol (20:20:1) mixture as mobile phase. The fractions 7560–8835 ml (A) and 8836–9360 ml (B) were collected and evaporated. The product from fraction A (128 mg) was identified with $^1$H-NMR and mass spectrometry to be (22S)-16α,17α-butylidenedioxy-9α-fluoro-11β,21-dihydroxypregn-4-ene-3,20-dione and the product from the B fraction (50 mg) as the 22R-epimer.

The epimers had the following properties. Epimer 22S: Melting point 180°–190° C.; $[\alpha]_D^{25}$=+105.6° (c=0.214; $CH_2Cl_2$); molecular weight 450 (calc. 450.6). Epimer 22R: Melting point 147°–151° C.; $[\alpha]_D^{25}$=+133.7° (c=0.196; $CH_2Cl_2$); molecular weight 450 (calc. 450.6). The purity of the epimers was determined by HPLC analysis to be 95.6% for the 22S-epimer and 98.2% for the 22R-epimer.

A solution of palmitoyl chloride (0.34 ml) in 5 ml of dioxane was added dropwise to a solution of (22R)-16α,17abutylidenedioxy-9α-fluoro-11β,21-dihydroxypregn-4-ene-3,20-dione (50 mg) in 10 ml of pyridine. The reaction mixture was stirred at room temperature overnight and worked up as in Example 1. The crude product was purified on a Sephadex LH-20 column (89×2.5 cm) using heptane:chloroform:ethanol, 20:20:1, as mobile phase. The fraction 180–205 ml was collected and evaporated, yielding 36 mg of (22R)-16α,17α-butylidenedioxy-9α-fluoro-11β-hydroxy-21-palmitoyloxypregn-4-ene-3,20-dione as an oil. Purity: 96.3% (HPLC-analysis). Molecular weight 688 (calc. 688.97).

Example 26

(22S)-16α,17α-Butylidenedioxy-9α-fluoro-11β-hydroxy-21-palmitoyloxypregn-4-ene-3,20-dione A solution of Palmitoyl chloride (0.14 ml) in 15 ml of dioxane was added dropwise to a solution of (22S)-16α,17abutylidenedioxy-9α-fluoro-11β,21-dihydroxypregn-4-ene-3,20-dione (41 mg) in 3 ml of pyridine. The reaction mixture was stirred at room temperature overnight and worked up as in Example 1. The crude product was purified on a Sephadex LH-20 column (89×2.5 cm) using heptane:chloroform:ethanol, 20:20:1, as mobile phase. The fraction 215–260 ml was collected and evaporated, yielding 26 mg of (22S)-16α,17α-butylidenedioxy-9α-fluoro-11β-hydroxy-21-palmitoyloxypregn-4-ene-3,20-dione as an oil. Purity: 91.4% (HPLC-analysis). Molecular weight 688 (calc. 688.97).

Example 27

(22R)-16α,17α-Butylidenedioxy-9α-fluoro-11β-hydroxy-21-palmitoyloxypregn-1,4-diene-3,20-dione A solution of palmitoyl chloride (75 mg) in 2.5 ml of dioxane was added dropwise to a solution of (22R)-16α,17abutylidenedioxy-9α-fluoro-11β,21-dihydroxypregna-1,4-diene-3,20-dione (25 mg) in 5 ml of pyridine. The reaction mixture was stirred at room temperature overnight and worked up as in Example 1. The crude product was purified on a Sephadex LH-20 column (85×2.5 cm) using chloroform as mobile phase. The fraction 235–285 ml was collected and evaporated, yielding 27 mg of (22R)-16α,17α-butylidenedioxy-9α-fluoro-11β-hydroxy-21-palmitoyloxypregna-1,4-diene-3,20-dione. Melting point 116°–121° C.; $[\alpha]_D^{25}$=+67.4° (c=0.172; $CH_2Cl_2$). Molecular weight 686 (calc. 687.0). Purity: 96.5% (HPLC-analysis).

Example 28

(22R)-16α,17α-Butylidenedioxy-21-caprylyloxy-6α,9α-difluoro-11β-hydroxypregn-4-ene-dione To a solution of (22R)-16α,17α-butylidenedioxy-6α,9α-difluoro-11β,21-dihydroxypregn-4-ene-3,20-dione (60 mg) in 4 ml of methylene chloride was added caprylyl chloride (35 mg) and 4-dimethylaminopyridine (30 mg). The reaction mixture was stirred at room temperature for 45 min. After evaporation the residue was purified by chromatography on a Merck Kieselgel 60 column using heptane:ethyl acetate, 1:1, as mobile phase. The product obtained was further purified by chromatography on a Sephadex LH-20 column (85×2.5 cm i.d.) using chloroform as mobile phase. The fraction 280–315 ml was collected and evaporated and the residue precipitated from methylene chloride:petroleum ether, yielding 28 mg of (22R)-16α,17α-butylidenedioxy-21-caprylyoxy-6α,9α-difluoro-11β-hydroxypregn-4-ene-3,20-dione. Melting point 158°–165° C. $[\alpha]_D^{25}$=+103.7° (c=0.216, $CH_2Cl_2$). Molecular weight 594 (calc. 594.7).

Example 29

(22R)-16α,17α-Butylidenedioxy-21-caproyloxy-6α,9α-difluoro-11β-hydroxypregn-4-ene-3,20-dione A solution of capryl chloride (75 mg) in 2 ml of dioxane was aded dropwise to a solution of (22R)-16α,17α-butylidenedioxy-6α,9α-difluoro-11β,21-dihydroxypregn-4-ene-3,20-dione (60 mg) in 4 ml of pyridine. The reaction mixture was stirred at room temperature overnight and worked up as in Example 1. The crude product was purified by chromatography on a Sephadex LH-20 column (89×2.5 cm i.d.) using heptane:chloroform:ethanol, 20:20:1, as mobile phase. The fraction 245–315 ml was collected and evaporated and the residue precipitated from methylene chloride:petroleum ether, yielding 58 mg of (22R)-16α,17α-butylidenedioxy-21-caprylyoxy-6α,9α-difluoro-11β-hydroxypregn-4-ene-3,20-dione. Melting point 168°–171° C. $[\alpha]_D^{25}$=+93.7° (c=0.302; $CH_2Cl_2$). Molecular weight 622 (calc. 622.8). Purity: 94.1% (HPLC-analysis).

Example 30

(22R)-16α,17α-Butylidenedioxy-21-caproyloxy-6α,9α-difluoro-11β-hydroxypregn-4-ene-3,20-dione To a solution of (22R)-16α,17α-butylidenedioxy-6α,9α-difluoro-11β,21-dihydroxypregn-4-ene-3,20-dione (60 mg) in 4 ml of methylene chloride was added caproyl chloride (25 mg) and 4-methylaminopyridine (30 mg). The reaction mixture was stirred at room temperature for 30 min and worked up as in Example 28. The product after chromatography on Merck Kieselgel 60 was further purified by chromatography on a Sephadex LH-20 column (85×2.5 cm i.d.) using chloroform as mobile phase. The fraction 300–345 ml was collected and evaporated and the residue precipitated from methylene chloride:petroleum ether, yielding 20 mg of (22R)-16α,17α-butylidenedioxy-21-caproyloxy-6α,9α-difluoro-11β-hydroxypregn-4-ene-3,20-dione. Melting point 148°–160° C. $[\alpha]_D^{25}$=+107.3° (c=0.232; $CH_2Cl_2$). Molecular weight 566 (calc. 566.7). Purity: 99.3% (HPLC-analysis).

Example 31

(22R)-16α,17α-Butylidenedioxy-6α, 9α-difluoro-11β-hydroxy-21-propionyloxypregn-4-ene-3,20-dione A solution of propionyl chloride (150 mg) in 5 ml of dioxane was added dropwise to a solution of (22R)-16α,17α-butylidenedioxy-6α,9α-difluoro-11β,21-dihydroxypregn-4-ene- 3,20-dione (150 mg) in 10 ml of pyridine. The reaction mixture was stirred at room temperature overnight and worked up as in Example 1. The crude product was purified by chromatography on a Sephadex LH-20 column (70×6.3 cm i.d.) using chloroform as mobile phase. The fraction 1485–1695 ml was collected and evaporated and further purified on a Sephadex LH-20 column (75×6.3 cm. i.d.) with heptane:chlorofrom:ethanol, 20:20:1, as mobile phase. The fraction 1925–2235 ml was collected and evaporated. The residue was precipitated from methylene chloride: petroleum ether, yielding 109 mg of (22R)-16α,17α-butylidenedioxy-6α,9α-difluoro-11β-hydroxy-21-propionyloxypregn-4-ene-3,20-dione. Melting point 206°–212° C. $[\alpha]_D^{25}$=+115.7° (c=0.216; $CH_2Cl_2$). Molecular weight 524 (calc. 524.6). Purity: 99.0% (HPLC-analysis).

Example 32

(22R)-16α,17α-Butylidenedioxy-21-butyryloxy-6α, 9α-difluoro-11β-hydroxy-pregn-4-ene 3,20-dione A solution of butyryl chloride (170 mg) in 5 ml of dioxane was added dropwise to a solution of (22R)-16α,17α-butylidenedioxy-6α,9α-difluoro-11β,21-dihydroxypregn-4-ene-3,20-dione (150 mg) in 10 ml of pyridine. The reaction mixture was stirred at room temperature overnight and worked up as in Example 1. The crude product was purified by chromatography on a Sephadex LH-20 column (70×6.3 cm i.d.) using chloroform as mobile phase. The fraction 1440–1740 ml was collected and evaporated and further purified on a Sephadex LH-20 column (75×6.3 cm i.d.) with heptane:chloroform:ethanol, 20:20:1, as mobile phase. The fraction 2010–2230 ml was collected and evaporated. The residue was precipitated from methylene chloride: petroleum ether, yielding 118 mg of (22R)-16α,17α-butylidenedioxy-21-butyryloxy-6α-9α-difluoro-11β-hydroxypregn-4-ene-3,20-dione. Melting point 208°–216° C. $[\alpha]_D^{25}$=+114.4° (c=0.216; $CH_2Cl_2$). Molecular weight 538 (calc. 538.6). Purity: 99.4% (HPLC-analysis).

Example 33

(22R)-16α,17α-Butylidenedioxy-6α, 9α-difluoro-11β-hydroxy-21-valeryloxypregn-4-ene 3,20-dione A solution of valeryl chloride (60 mg) in 5 ml of dioxane was added dropwise to a solution of (22R)-16α,17α-butylidenedioxy-6α,9α-difluoro-11β,21-dihydroxypregn-4-ene-3,20-dione (75 mg) in 5 ml of pyridine. The reaction mixture was stirred at room temperature overnight and worked up as in Example 1. The crude product was purified by chromatography on a Sephadex LH-20 column (85×2.5 cm i.d.) with chloroform as mobile phase. The fraction 265–325 ml was dissolved in methylene chloride and precipitated by petroleum ether, yielding 52 mg of (22R)-16α, 17α-butylidenedioxy- 6α,9α-difluoro-11β-hydroxy-21-valeryloxypregn-4-ene-3,20-dione. Melting point 181°–185° C. $[\alpha]_D^{25}$=+109.4° (c=0.212; $CH_2Cl_2$). Molecular weight 552 (calc. 552.7). Purity: 99.8% (HPLC-anaylsis).

Example 34

Pharmaceutical Preparations

The following nonlimiting examples illustrate formulations intended for different topical forms of administration. The amount of active steroid in the percutaneous formulations is ordinarily 0.001–0.2% (w/w), preferably 0.01–0.1% (w/w).

Formulation 1, Ointment
  Steroid, micronized 0.025 g
  Liquid paraffin 10.0 g
  White soft paraffin ad 100.0 g
Formulation 2, Ointment
  Steroid 0.025 g
  Propylene glycol 5.0 g
  Sorbitan sesquioleate 5.0 g
  Liquid paraffin 10.0 g
  White soft paraffin ad 100.0 g
Formulation 3, Oil in water cream
  Steroid 0.025 g
  Cetanol 5.0 g
  Glyceryl monostearate 5.0 g
  Liquid paraffin 10.0 g
  Cetomacrogol 1000 2.0 g
  Citric acid 0.1 g
  Sodium citrate 0.2 g
  Propylene glycol 35.0 g
  Water ad 100.0 g
Formulation 4, Oil in water cream
  Steroid, micronized 0.025 g
  White soft paraffin 15.0 g
  Liquid paraffin 5.0 g
  Cetanol 5.0 g
  Sorbimacrogol stearate 2.0 g
  Sorbitan monostearate 0.5 g
  Sorbic acid 0.2 g
  Citric acid 0.1 g
  Sodium citrate 0.2 g
  Water ad 100 g
Formulation 5, Water in oil cream
  Steroid 0.025 g
  White soft paraffin 35.0 g
  Liquid paraffin 5.0 g
  Sorbitan sesquioleate 5.0 g
  Sorbic acid 0.2 g
  Citric acid 0.1 g
  Sodium citrate 0.2 g
  Water ad 100.0 g
Formulation 6, Lotion
  Steroid 0.25 mg
  Isopropanol 0.5 ml
  Carboxyvinylpolymer 3 mg
  NaOH q.s.
  Water ad 1.0 g
Formulation 7, Suspension for injection
  Steroid, micronized 0.05–10 mg
  Sodium carboxymethylcellulose 7 mg
  NaCl 7 mg
  Polyoxyethylene (20) sorbitan monooleate 0.5 mg
  Phenyl carbinol 8 mg
  Water, sterile ad 1.0 ml Formulation 8, Aerosol for oral and nasal inhalation
  Steroid, micronized 0.1% W/W
  Sorbitan trioleate 0.7% w/w
  Trichlorofluoromethane 24.8% W/W Dichlorotetrafluoroethane 24.8% W/W Dichlorodifluoromethane 49.6% W/W Formulation 9, Solution for atomization Steroid 7.0 mg Propylene glycol 5.0 g Water ad 10.0 g Formulation 10, Powder for inhalation A gelatin capsule is filled with a mixture of Steroid, micronized 0.1 mg Lactose 20 mg The powder is inhaled by means of an inhalation device.

Formulation 11, Powder for inhalation

The spheronized powder is filled into a multidose powder inhaler. Each dose contains Steroid, micronized 0.1 mg Formulation 12, Powder for inhalation The spheronized powder is filled into a multidose powder inhaler. Each dose contains Steroid, micronized 0.1 mg Lactose, micronized 1 mg Formulation 13, capsule for treating the small bowel Steroid 1.0 mg Sugar spheres 321 mg Aquacoat ECD 30 6.6 mg Acetyltributyl citrate 0.5 mg Polysorbate 80 0.1 mg Eudragit L100-55 17.5 mg Triethylcitrate 1.8 mg Talc 8.8 mg Antifoam MMS 0.01 mg Formulation 14, capsule for treating the large bowel Steroid 2.0 mg Sugar spheres 305 mg Aquacoat ECD 30 5.0 mg Acetyltributyl citrate 0.4 mg Polysorbate 80 0.14 mg Eudragit NE30 D 12.6 mg Eudragit S100 12.6 mg Talc 12.6 mg Formulation 15, rectal enema Steroid 0.02 mg Sodium carboxymethylcellulose 25 mg Disodium edetate 0.5 mg Methyl parahydroxybenzoate 0.8 mg Propyl parahydroxybenzoate 0.2 mg Sodium chloride 7.0 mg Citric acid anhydrous 1.8 mg Polysorbate 80 0.01 mg Water, purified ad 1.0 ml Formulation 16, formulation containing liposome-bound steroid A. Preparation of a formulation for instillation Synthetic dipalmitoylphosphatidylcholine (45 mg), dimyristoylphosphatidylcholine (7 mg), dipalmitoylphosphatidylglycerol (1 mg) and (22R)-16α,17α-butylidenedioxy-6α,9α-difluoro-11β-hydroxy-21-palmitoyloxypregn-4-ene-3,20-dione (5 mg) are mixed in a glass tube. All components are dissolved in chloroform. Most of the solvent is evaporated by the use of $N_2$ and then under reduced pressure, which allows formation of a thin film of the lipid components on the surface of the glass tube. An aqueous solution (0.9% NaCl) is added to the lipids. Formation of the liposomes is performed at a temperature above the phase transition temperature of the lipids. The liposomes are formed by shaking or sonication of the solution with the probe of a sonicator. The resulting suspension contains liposomes ranging from very small vesicles to 2 μm in size.

B. Preparation of a formulation for inhalation

The preparation of the liposomes is performed according to Example A, wherein the aqueous solution contains 10% lactose. The ratio between lactose and lipid is 7:3. The liposome suspension is frozen on dry ice and lyophilized. The dry product is micronized, resulting in particles with a mass mean aerodynamic diameter (MMAD) of about 2 μm.

Pharmacology

The selectivity for local anti-inflammatory activity can be exemplified by the following airway model.

A considerable fraction of inhaled GCS is deposited in the pharynx and is subsequently swallowed, ending up in the gut. This fraction contributes to the unwanted side effects of the steroid since it is acting outside the area (the lung) intended for treatment. Therefore, it is favourable to use a GCS with high local anti-inflammatory activity in the lung but low GCS-induced effects after oral administration. Studies were therefore done in order to determine the GCS-induced effects after local application in the lung as well as after peroral administration, and the differentiation between glucocorticosteroid actions in the treated lung region and outside this area was tested in the following way.

Test models

A) Test model for desired local antiinflammatory activity on airway mucosa (left lung lobe).

Sprague Dawley rats (250 g) were slightly anaesthetized. with Ephrane and the glucocorticosteroid test preparation (in liposomes suspended in saline) in a volume of 0.5 ml/kg was instilled into the left lung lobe only. Two hours later a suspension of Sephadex (5 mg/kg in a volume of 1 ml/kg) was instilled in the trachea well above the bifurcation so that the suspension reached both the left and right lung lobes. Twenty hours later the rats were killed and the left lung lobes dissected out and weighed. Control groups got vehicle instead of glucocorticosteroid preparation and saline instead of Sephadex suspension so that lung weight due to non-drug-treated, Sephadex-induced edema and the normal lung weight could be determined.

B) Test model for unwanted systemic effect by orally absorbed glucocorticosteroid Sprague Dawley rats (250 g) were slightly anaesthetized with Ephrane and the GCS test preparation in a volume of 1.0 ml/kg was given orally. Two hours later a suspension of Sephadex (5 mg/kg in a volume of 1 ml/kg) was instilled in the trachea well above the bifurcation so that the suspension reached both the left and the right lung lobes. Twenty hours later, the rats were killed and the lung lobes were weighed. Control groups got vehicle instead of glucocorticosteroid preparation and saline instead of Sephadex suspension so that lung weight due to non-drug-treated, Sephadex-induced edema and the normal lung weight could be determined.

The results of the comparative study are given in Table 1. The pharmacological profiles of the compounds of the invention were compared to those of budesonide-21-palmitate and flumethasone-21-palmitate in liposomes. All tested steroids of the invention show higher local anti-inflammatory potency in the lung after local application than budesonide-21-palmitate in liposomes. Furthermore, the results also demonstrate a higher lung selectivity of the tested compounds of the invention compared to the selected prior art compounds, since the dose required to inhibit lung edema ($ED_{50}$) by oral administration of the above mentioned compounds are 158 (example 3), 247 (example 7) and 559 (example 1) times higher and of budesonide-21-palmitate 66 times higher and of flumethasone-21-palmitate 8 times higher than the respective doses needed to inhibit lung edema by local application to the lung of the drugs.

Thus it can be concluded that the compounds of the invention are well suited for local treatment of inflammatory disorders in the skin and various cavities of the body (e.g. lung, nose, bowel and joint).

TABLE 1

Effects of tested glucocorticosteroids in liposomes in the Sephadex induced lung edema model in the rat. The results are given in relation to the corresponding control group given Sephadex.

| Compound according to example | $ED_{50}$ (left lung administration; nmol/kg) Left lung lobe[x] | $ED_{50}$ (p.o. adm.; nmol/kg) lung[x] | Ratio oral/local administration |
|---|---|---|---|
| Budesonide-21-palmitate (RS) | 23 | 1520 | 66 |
| Flumethasone-21-palmitate | 2.2 | 18 | 8 |
| 7 | 2.3 | 568 | 247 |
| 6 | 1.8 | — | — |
| 3 | 3.5 | 554 | 158 |
| 1 | 1.5 | 839 | 559 |

[x]$ED_{50}$ = required glucocorticosteroid dose to reduce the edema by 50%.

We claim:

1. A compound of the formula

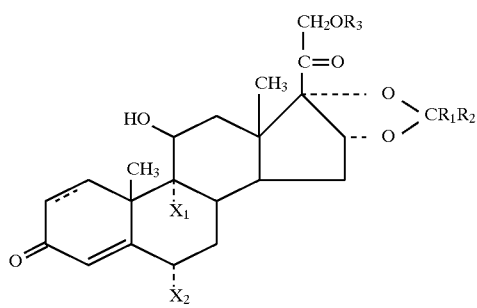

or a stereoisomeric component thereof, in which formula the 1,2-position is saturated or is a double bond;

$R_1$ is hydrogen;

$R_2$ is a straight or branched hydrocarbon chain having 1–10 carbon atoms;

$R_3$ is acyl having a straight or branched, saturated or unsaturated hydrocarbon chain having 11–20 carbon atoms;

$X_1$ is flourine; and $X_2$ is fluorine.

2. A compound of the formula

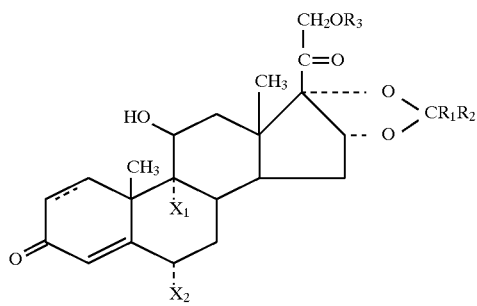

or a stereoisomeric component thereof, in which formula the 1,2-position is saturated or is a double bond;

$R_1$ is hydrogen;

$R_2$ is a straight or branched hydrocarbon chain having 2–10 carbon atoms;

$R_3$ is acyl having a straight or branched, saturated or unsaturated hydrocarbon chain having 11–20 carbon atoms;

$X_1$ is fluorine; and $X_2$ is fluorine.

3. A compound of the formula

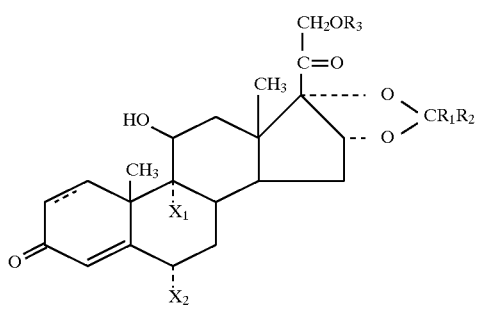

or a stereoisomeric component thereof, in which formula the 1,2-position is saturated or is a double bond;

$R_1$ is hydrogen;

$R_2$ is a straight or branched hydrocarbon chain having 1–10 carbon atoms;

$R_3$ is acyl having a straight or branched, saturated or unsaturated hydrocarbon chain having 13–20 carbon atoms;

$X_1$ is fluorine; and $X_2$ is fluorine.

4. A compound according to claim 3 wherein $R_3$ has 14–18 carbon atoms.

5. A compound according to claim 1, 2, 3 or 4, wherein the 1,2-position is saturated.

6. A compound according to claim 5 wherein $R_2$ is propyl.

7. A compound according to claim 1 or 2 wherein the 1,2-position is a double bond, $R_2$ is propyl, and $R_3$ is palmitoyl.

8. A compound according to claim 5 which is a 21-ester of (22R)-16α,17α-butylidenedioxy-6α,9α-difluoro-11β,21-dihydroxy pregna-4-ene-3,20-dione.

9. A compound according to claim 1, 2, 3 or 4, which is a 21-ester of (22R)-16α,17α-butylidenedioxy-6α,9α-difluoro-11β,21-dihydroxypregna-1,4-diene-3,20-dione.

10. A pharmaceutical composition comprising as active ingredient a compound according to claim 1, 2, 3 or 4 in a pharmaceutically acceptable carrier.

11. A pharmaceutical composition according to claim 10 in liposome form.

12. A pharmaceutical composition according to claim 11 in dosage unit form.

13. A method for the treatment of inflammatory and allergic conditions in a mammal in need of such treatment, which comprises administering to the mammal an effective amount of a compound according to claim 1, 2, 3 or 4.

14. A compound according to claim 1, 2, 3 or 4, wherein the 1,2-position is a double bond.

* * * * *